US010806525B2

(12) United States Patent
McGinley et al.

(10) Patent No.: US 10,806,525 B2
(45) Date of Patent: Oct. 20, 2020

(54) SURGICAL INSTRUMENT WITH REAL TIME NAVIGATION ASSISTANCE

(71) Applicant: McGinley Engineered Solutions, LLC, Casper, WY (US)

(72) Inventors: Joseph C. McGinley, Casper, WY (US); Michael Andrew Swartz, San Jose, CA (US); Thomas Edward Stout, San Jose, CA (US); Mike Zelina, Lakewood, OH (US); Collin T. Stoner, San Leandro, CA (US)

(73) Assignee: McGinley Engineered Solutions, LLC, Casper, WY (US)

( * ) Notice: Subject to any disclaimer, the term of this patent is extended or adjusted under 35 U.S.C. 154(b) by 0 days.

(21) Appl. No.: 16/342,154

(22) PCT Filed: Oct. 2, 2018

(86) PCT No.: PCT/US2018/053993
§ 371 (c)(1),
(2) Date: Apr. 15, 2019

(87) PCT Pub. No.: WO2019/070729
PCT Pub. Date: Apr. 11, 2019

(65) Prior Publication Data
US 2019/0231443 A1 Aug. 1, 2019

Related U.S. Application Data

(60) Provisional application No. 62/566,655, filed on Oct. 2, 2017, provisional application No. 62/618,427, filed on Jan. 17, 2018.

(51) Int. Cl.
*A61B 5/05* (2006.01)
*A61B 34/20* (2016.01)
(Continued)

(52) U.S. Cl.
CPC ............ *A61B 34/20* (2016.02); *A61B 34/25* (2016.02); *A61B 34/30* (2016.02); *A61B 90/06* (2016.02);
(Continued)

(58) Field of Classification Search
None
See application file for complete search history.

(56) References Cited

U.S. PATENT DOCUMENTS 1,831,813 A 11/1931 Levedahl
2,883,891 A 4/1959 Robinson et al.
(Continued)

FOREIGN PATENT DOCUMENTS

DE 102011056927 6/2013
WO 9724991 7/1997
(Continued)

*Primary Examiner* — Joel F Brutus
(74) *Attorney, Agent, or Firm* — Holzer Patel Drennan

(57) ABSTRACT

Navigation assistance systems and methods for use with a surgical instrument to assist in navigation of a surgical instrument during an operation. The system may include sensors that may observe the patient to generate positioning data regarding the relative position of the surgical instrument and the patient. The system may retrieve imaging data regarding the patient and correlate the imaging data to the positioning data. In turn, the position of the surgical instrument relative to the imaging data may be provided and used to generate navigation date (e.g., position, orientation, trajectory, or the like) regarding the surgical instrument.

29 Claims, 8 Drawing Sheets

(51) Int. Cl.
*A61B 90/00* (2016.01)
*A61B 34/00* (2016.01)
*A61B 34/30* (2016.01)
A61B 90/50 (2016.01)
A61B 34/10 (2016.01)
A61B 5/06 (2006.01)
A61B 17/00 (2006.01)

(52) U.S. Cl.
CPC .............. *A61B 90/37* (2016.02); *A61B 5/061* (2013.01); *A61B 2017/00123* (2013.01); *A61B 2034/107* (2016.02); *A61B 2034/2048* (2016.02); *A61B 2034/2051* (2016.02); *A61B 2034/2057* (2016.02); *A61B 2034/2063* (2016.02); *A61B 2034/2065* (2016.02); *A61B 2034/254* (2016.02); *A61B 2090/062* (2016.02); *A61B 2090/064* (2016.02); *A61B 2090/365* (2016.02); *A61B 2090/367* (2016.02); *A61B 2090/372* (2016.02); *A61B 2090/374* (2016.02); *A61B 2090/376* (2016.02); *A61B 2090/3762* (2016.02); *A61B 2090/3925* (2016.02); *A61B 2090/3966* (2016.02); *A61B 2090/502* (2016.02)

(56) References Cited

U.S. PATENT DOCUMENTS

| | | |
|---|---|---|
| 3,804,544 A | 4/1974 | Adams |
| 4,014,621 A | 3/1977 | Johnson et al. |
| 4,063,356 A | 12/1977 | Hepworth |
| 4,157,231 A | 6/1979 | Phillips |
| 4,310,269 A | 1/1982 | Neu et al. |
| 4,329,092 A | 5/1982 | Ponitzsch et al. |
| 4,329,095 A | 5/1982 | Schmuck |
| 4,644,335 A | 2/1987 | Wen |
| 4,710,075 A | 12/1987 | Davison |
| 4,723,911 A | 2/1988 | Kurtz |
| 4,765,333 A | 8/1988 | Bray |
| 4,867,158 A | 9/1989 | Sugg |
| 4,951,690 A | 8/1990 | Baker |
| 5,013,194 A | 5/1991 | Wienhold |
| 5,014,793 A | 5/1991 | Germanton et al. |
| 5,022,798 A | 6/1991 | Eckman |
| 5,071,293 A | 12/1991 | Wells |
| 5,133,728 A | 7/1992 | Petersen |
| 5,139,376 A | 8/1992 | Pumphrey |
| 5,161,921 A | 11/1992 | Corsi |
| 5,277,799 A | 1/1994 | Bransch |
| 5,361,504 A | 11/1994 | Huang |
| 5,380,333 A | 1/1995 | Meloul et al. |
| 5,411,503 A | 5/1995 | Hollstein et al. |
| 5,533,842 A | 7/1996 | Johnson et al. |
| 5,538,423 A | 7/1996 | Coss et al. |
| 5,584,838 A | 12/1996 | Rona et al. |
| 5,599,142 A | 2/1997 | Fujimoto et al. |
| 5,613,810 A | 3/1997 | Bureller |
| 5,810,828 A | 9/1998 | Lightman et al. |
| 5,902,306 A | 5/1999 | Norman |
| 5,961,257 A | 10/1999 | Bettini et al. |
| 5,980,248 A | 11/1999 | Kusakabe et al. |
| 6,033,409 A | 3/2000 | Allotta |
| 6,081,741 A | 6/2000 | Hollis |
| 6,096,042 A | 8/2000 | Herbert |
| 6,342,057 B1 | 1/2002 | Brace et al. |
| 6,494,590 B1 | 12/2002 | Paganini |
| 6,527,778 B2 | 3/2003 | Athanasiou et al. |
| 6,587,184 B2 | 7/2003 | Wursch et al. |
| 6,665,948 B1 | 12/2003 | Kozin et al. |
| 6,786,683 B2 | 9/2004 | Schaer et al. |
| D502,798 S | 3/2005 | Belley et al. |
| 6,925,725 B2 | 8/2005 | Herrmann et al. |
| 7,073,989 B2 | 7/2006 | Erickson et al. |
| 7,185,998 B2 | 3/2007 | Oomori |
| 7,220,088 B2 | 5/2007 | Ferrari et al. |
| 7,235,940 B2 | 6/2007 | Bosch et al. |
| 7,314,048 B2 | 1/2008 | Couture et al. |
| 7,482,819 B2 | 1/2009 | Wuersch |
| 7,578,642 B2 | 8/2009 | Fritsche et al. |
| 7,681,659 B2 | 3/2010 | Zhang et al. |
| 7,691,106 B2 | 4/2010 | Schenberger |
| 7,840,253 B2 | 11/2010 | Tremblay |
| 7,946,049 B1 | 5/2011 | Wilton |
| 7,992,311 B2 | 8/2011 | Cerwin |
| 8,092,457 B2 | 1/2012 | Oettinger |
| 8,162,074 B2 | 4/2012 | Cook |
| 8,167,518 B2 | 5/2012 | Mathis et al. |
| 8,171,642 B2 | 5/2012 | Fritsche |
| 8,317,437 B2 | 11/2012 | Merkley et al. |
| 8,460,297 B2 | 6/2013 | Watlington |
| 8,511,945 B2 | 8/2013 | Apkarian |
| 8,734,153 B2 | 5/2014 | Arzanpour |
| 8,821,493 B2 | 9/2014 | Anderson |
| 8,894,654 B2 | 11/2014 | Anderson |
| 8,925,169 B2 | 1/2015 | Schevers |
| 8,970,207 B2 | 3/2015 | Baumgartner |
| 9,022,949 B2 | 5/2015 | Herndon |
| 9,114,494 B1 | 8/2015 | Mah |
| 9,204,885 B2 | 12/2015 | McGinley |
| 9,358,016 B2 | 6/2016 | McGinley |
| 9,370,372 B2 | 6/2016 | McGinley |
| 9,492,181 B2 | 11/2016 | McGinley |
| 9,826,984 B2 | 11/2017 | McGinley et al. |
| 9,855,060 B2 | 1/2018 | Ardel |
| 2001/0031919 A1 | 10/2001 | Strommer |
| 2001/0047219 A1 | 11/2001 | Oden |
| 2002/0165549 A1 | 11/2002 | Owusu-Akyaw et al. |
| 2003/0049082 A1 | 3/2003 | Morrison |
| 2003/0229351 A1 | 12/2003 | Tidwell |
| 2004/0097948 A1 | 5/2004 | Heldreth |
| 2004/0146367 A1 | 7/2004 | Gerhardt |
| 2004/0179829 A1 | 9/2004 | Phillips et al. |
| 2004/0215395 A1 | 10/2004 | Strasser |
| 2005/0116673 A1 | 6/2005 | Carl |
| 2005/0131415 A1 | 6/2005 | Hearn et al. |
| 2005/0169717 A1 | 8/2005 | Field |
| 2005/0261870 A1 | 11/2005 | Cramer |
| 2006/0004371 A1 | 1/2006 | Williams et al. |
| 2006/0008771 A1 | 1/2006 | Courvoisier |
| 2006/0025677 A1* | 2/2006 | Verard ................. A61B 90/36 600/423 |
| 2006/0074292 A1 | 4/2006 | Thomson |
| 2006/0241628 A1 | 10/2006 | Parak |
| 2006/0258938 A1* | 11/2006 | Hoffman ............ A61B 1/00193 600/424 |
| 2007/0030486 A1 | 2/2007 | Gelbart |
| 2007/0035311 A1 | 2/2007 | Wuersch |
| 2007/0041799 A1 | 2/2007 | Schaefer |
| 2008/0119725 A1* | 5/2008 | Lloyd .................... A61B 90/36 600/424 |
| 2008/0167653 A1 | 7/2008 | Watlington |
| 2008/0226409 A1 | 9/2008 | Hasenzahl |
| 2008/0228195 A1 | 9/2008 | von Jako |
| 2008/0243125 A1 | 10/2008 | Guzman |
| 2008/0292416 A1 | 11/2008 | Kado et al. |
| 2009/0131986 A1 | 5/2009 | Lee et al. |
| 2009/0182226 A1* | 7/2009 | Weitzner .................. A61B 6/12 600/424 |
| 2009/0245956 A1 | 10/2009 | Apkarian et al. |
| 2009/0299439 A1 | 12/2009 | Mire et al. |
| 2009/0326537 A1 | 12/2009 | Anderson |
| 2010/0114099 A1 | 5/2010 | Patwardhan |
| 2010/0137874 A1 | 6/2010 | Kim et al. |
| 2010/0239380 A1 | 9/2010 | Amirov et al. |
| 2011/0020084 A1 | 1/2011 | Brett |
| 2011/0060242 A1 | 3/2011 | Hausman |
| 2011/0245831 A1 | 10/2011 | Giersch |
| 2011/0245832 A1 | 10/2011 | Giersch et al. |
| 2011/0245833 A1 | 10/2011 | Anderson |
| 2011/0301611 A1 | 12/2011 | Garcia et al. |
| 2012/0037386 A1 | 2/2012 | Cook |
| 2012/0123418 A1 | 5/2012 | Giurgi |
| 2012/0179070 A1 | 7/2012 | Pommer et al. |

(56) References Cited

U.S. PATENT DOCUMENTS

| | | |
|---|---|---|
| 2012/0253348 A1 | 10/2012 | Arlettaz et al. |
| 2013/0122466 A1 | 5/2013 | Connor |
| 2013/0237811 A1 | 9/2013 | Mihailescu |
| 2013/0304069 A1 | 11/2013 | Bono et al. |
| 2013/0307529 A1 | 11/2013 | Baumgartner |
| 2013/0327552 A1 | 12/2013 | Lovelass |
| 2014/0039517 A1 | 2/2014 | Stryker |
| 2014/0081659 A1* | 3/2014 | Nawana ............ G16Z 99/00 705/3 |
| 2014/0107471 A1 | 4/2014 | Haider |
| 2014/0275760 A1 | 9/2014 | Lee |
| 2014/0275989 A1* | 9/2014 | Jacobsen ............ A61B 5/061 600/424 |
| 2014/0350685 A1 | 11/2014 | Bagga |
| 2015/0066030 A1 | 3/2015 | McGinley |
| 2015/0066035 A1 | 3/2015 | McGinley |
| 2015/0066036 A1 | 3/2015 | McGinley |
| 2015/0066037 A1 | 3/2015 | McGinley |
| 2015/0066038 A1 | 3/2015 | McGinley et al. |
| 2015/0165580 A1 | 6/2015 | Holland |
| 2016/0120553 A1 | 5/2016 | Xie |
| 2016/0247276 A1 | 8/2016 | Chou |
| 2017/0128081 A1 | 5/2017 | McGinley |
| 2017/0143396 A1 | 5/2017 | McGinley |
| 2017/0245868 A1 | 8/2017 | McGinley |
| 2017/0345398 A1 | 11/2017 | Fuchs |
| 2018/0070113 A1 | 3/2018 | Phillips |
| 2018/0110572 A1 | 4/2018 | Flatt |
| 2018/0260931 A1 | 9/2018 | Ozguner |
| 2019/0209287 A1 | 7/2019 | Zenz-Olson |

FOREIGN PATENT DOCUMENTS

| | | |
|---|---|---|
| WO | 2015006296 | 1/2015 |
| WO | 2015014771 | 2/2015 |
| WO | 2015034562 | 3/2015 |
| WO | 2016207628 | 12/2016 |

* cited by examiner

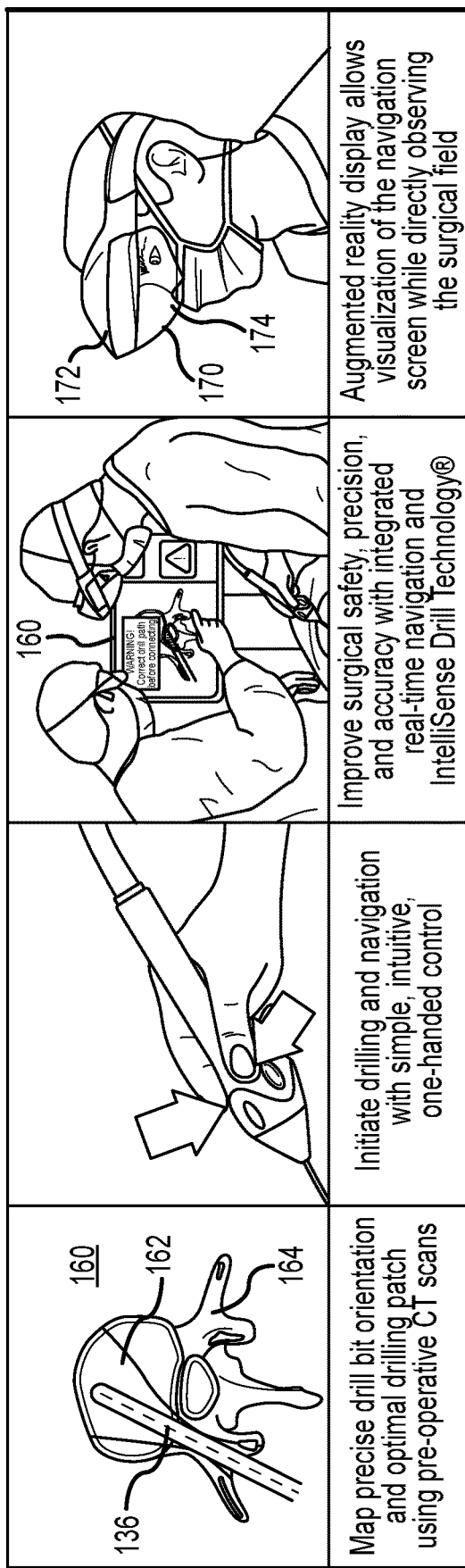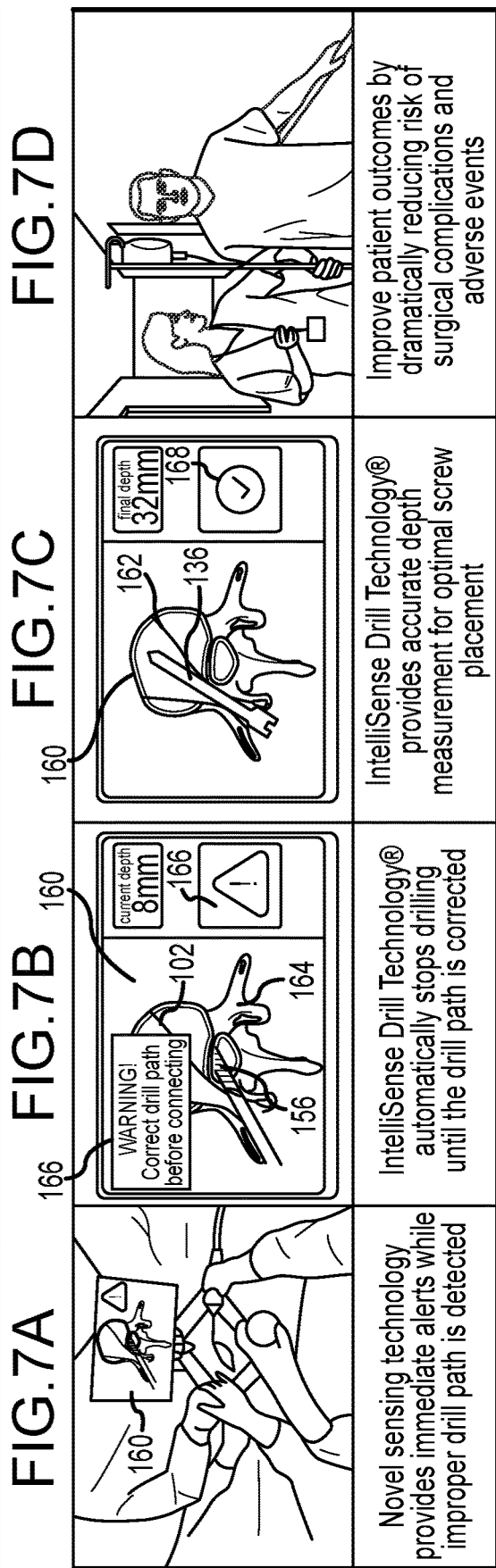

SURGICAL INSTRUMENT WITH REAL TIME NAVIGATION ASSISTANCE

RELATED APPLICATIONS

This application is a National Stage Application under 37 CFR 371 of PCT Application No. PCT/US2018/053993 filed on Oct. 2, 2018 entitled "SURGICAL INSTRUMENT WITH REAL TIME NAVIGATION ASSISTANCE", which claims the benefit of U.S. Application No. 62/618,427 filed on Jan. 17, 2018 entitled "SURGICAL INSTRUMENT WITH REALTIME NAVIGATION ASSISTANCE" and U.S. Application No. 62/566,655 filed on Oct. 2, 2017 entitled "SURGICAL INSTRUMENT WITH REALTIME NAVIGATION ASSISTANCE", the entirety of which is incorporated by reference herein.

FIELD

The present disclosure relates to systems for use in surgical operations to monitor a surgical instrument prior to or during an operation.

BACKGROUND

The use of powered surgical instruments is common in many surgical procedures. Examples of such instruments may include drills, saws, grinders, or the like that may be electric, pneumatic, hydraulic, or otherwise powered. Often times, use of such powered surgical instruments may allow for more efficient surgical operations, thus resulting in reduced risk to the patient, improved efficiency for the surgeon, lower costs, and improved outcomes.

However, while such powered surgical instruments may provide advantages over human powered instruments, there may also be risk for inadvertent damage to the anatomy of the patient when using powered instruments. Specifically, certain anatomical structures of a patient may be vulnerable to being inadvertently damaged by powered surgical instruments. In this regard, it is important for a surgeon to accurately determine the placement and location of the surgical instrument before and during an operation.

In addition, medical imaging technology has improved the ability for a surgeon to accurately image the anatomy of the patient. However, despite the advances in imaging technology, it remains difficult for a surgeon to utilize such imaging during an operation. For instance, a pre-surgical imaging study may be conducted that may be reviewed by a surgeon prior to an operation. This imaging study may provide the surgeon valuable information regarding patient anatomy to assist the surgeon in planning the operation. However, beyond use in planning, the imaging study may provide little or no detail to the surgeon when actually performing a surgery using a powered instrument without subsequent imaging during the operation. Requiring further imaging during an operation to assist with instrument placement potentially exposes the patient to increased radiation, requires additional time, and may increase the overall risk associated with the operation. As such, there remains a need to improve the ability to provide guidance data to a surgeon using a surgical instrument in an operation.

SUMMARY

In view of the foregoing, the present disclose relates to use of sensors to detect the position of a surgical instrument relative to a patient for generation navigation data for use in operation of the surgical instrument. One or more sensors may be provided relative to the surgical instrument that sense a position of the surgical instrument relative to the patient to provide positioning data. The position data may provide information regarding the position and orientation of the surgical instrument relative to the patient. Specifically, the sensors may be operative to sense one or more reference anatomical features of the patient that allow the relative position of the surgical instrument to the patient to be determined. For instance, the reference anatomical features of the patient may correspond to visible portions of the patient. Such visible portions may correspond to internal or external anatomy. Preferably, the reference anatomical feature is dimensionally stable such that the reference anatomical feature may be reliably and repeatably sensed by the sensor.

Accordingly, imaging data corresponding to an imaging study of the patient may also be retrieved. The imaging data may be correlated with the positioning data. This may allow a navigation module or the like to determine navigation data corresponding to the relative position of the surgical instrument with respect to features within the imaging data. Specifically, the imaging data may include imaged anatomical features of the patent. The imaged anatomical features may not be visible from an exterior of the patient. In this regard, the imaged anatomical features may not otherwise be visible or visualized by a user in the absence of medical imaging data. However, by correlating the imaging data to the positioning data, the relative position of the surgical instrument may be determined relative to the portion patient represented by the imaging data. That is, once the imaging data is correlated to the positioning data, the relative position of the surgical instrument may be provided relative to both the reference anatomical feature of the patient as determined by the sensors and the imaged anatomical features described by the imaging data. As such, the relative position, orientation, trajectory, or the like may be provided regarding the surgical instrument relative to the imaged anatomical structures in the navigation data.

As the sensors may be operative to continually sense the position of the surgical instrument in real time, the navigation data corresponding to the positioning of the surgical instrument relative to the patient described by the imaging data may also be provided in substantially real time. This may allow a user (e.g., a surgeon) to determine instrument placement and/or trajectory of the surgical instrument relative to internal, non-visible anatomical features of the patient in a non-invasive manner (e.g., prior to initiating an operation). In addition, the correlation of the imaging data to the positioning data may allow the placement and/or trajectory of the instrument to be determined or confirmed without having to initiate a subsequent imaging study during the operation. Further still, the placement, orientation, and/or trajectory of the surgical instrument may be monitored such that if a condition in which the instrument is out of position, off course, or otherwise at risk of causing damage to surrounding tissue, the operation of the surgical instrument can be terminated. In this regard, operation may be conditioned on proper position, orientation, and/or trajectory such that the surgical instrument may not be operable until and unless the instrument in an acceptable position, orientation, and/or trajectory. Moreover, because the sensors may continually sense the position of the surgical instrument (e.g., in real time), the position of the patient may be monitored such that any change in position of the patient may be compensated for in the navigation data. That is, even if the patient moves, the sensors may be operative to update the position of the surgical instrument relative to the patient such that the navigation data is updated in response to the movement.

A number of different types of sensors are contemplated for use in connection with the disclosure provided herein. For example, the sensors may include ultrasonic sensors, infrared sensors, laser sensor, inertial sensors, mechanical sensors, optic sensors, and/or combinations thereof. The sensors may employ various approaches of operation. For instance, the ultrasonic, infrared, and/or laser sensors may utilize time-of-flight determination for generating positioning data. Moreover, the optic sensor may include a stereo-optic sensor, a structured light sensor, a light field lens sensor, and/or may be a time-of-flight sensor. Moreover, various combinations of sensors may be utilized without limitation. In this regard, while a number of specific sensor combinations are described herein, it is intended that this discussion be illustrative and not limiting. Additionally, in preferred embodiments, the sensors may be non-contact sensors that do not result in additional contact with the patient beyond that of the tool portion of the instrument.

In an embodiment, the sensors may be disposed on the surgical instrument to observe an area adjacent to the surgical instrument. For instance, a plurality of sensors may be disposed about the surgical instrument such that a collective field of observation of the plurality of sensors extends about all or substantially all of the surgical instrument. In this regard, as the surgical instrument is brought near the patient, the sensors may detect the location and/or orientation of the patient relative to the surgical instrument to generate positioning data. This may be accomplished by recognition of external, or externally visible, anatomical features of the patient.

Based on the location and/or orientation of the patient relative to the surgical instrument, imaging data that includes imaged anatomical features (e.g., which may include internal or non-visible anatomical features) may be correlated with the positioning data. That is, the imaging data may also include features corresponding to the portion of the patient observed by the plurality of sensors. In turn, common features (e.g., observable or external anatomical features) to those observed by the sensors (e.g., a reference anatomical feature) and those described in the imaging data (e.g., an imaged anatomical feature) may be aligned. The alignment or correlation of the imaging data to the positioning data may allow the navigation module to provide navigation data that relates the position and/or orientation surgical instrument to the imaging data. This may allow, for example prior to initiating an action with the surgical instrument, a determination of the position and/or trajectory of the surgical instrument relative to the internal or non-visible anatomical features described in the imaging data.

The present disclosure describes anatomical features as potentially "external" or "internal" features. Alternatively, certain features may be described as "visible" or "non-visible." In this regard, an external or visible anatomical feature may be visually perceptible from an exterior of a patient. In some contexts, this may correspond to the exterior of the skin of the patient and/or may include anatomic features such as appendages, or other landmarks that are visible from the exterior of the patient. Examples of such external or visible features may include appendages such as arms, legs, fingers, toes, or the like. Other external or visible features may include landmarks such as the navel or other visible landmark. Further still, such external or visible features may simply correspond to a discernable contour in the skin of the patient. Further still, a "visible" feature may comprise an anatomical structure below the skin that is perceivable by a user (e.g., a bone that is visible through the skin such as bones in the knee, ankle, shoulder, or the like). That is, external or visible features may correspond with subcutaneous features that can be discerned through the skin. For instance, the outline of a patient's patella may be discerned external to the patient's leg and may serve as a reference. In contrast, internal or non-visible features may correspond to, in at least some contexts, subcutaneous features that are not visible from the exterior of the patient. The external or visible features may comprise reference anatomical features that may be perceived by a sensor. Preferably such anatomical features are dimensionally stable for repeatable and reliable determination.

Internal or non-visible features may be imaged using medical imaging techniques described herein. As such, by non-visual, it is meant that the features are not visible by a user exterior to the patient rather than implying that the features cannot be imaged. Rather, the features may be captured in imaging data using a medical imaging technique described herein for review by a user to provide guidance as to the internal or non-visible features that are otherwise not visible by the user without the assistance of the imaging data.

As may be appreciated, common features may be identified in the positioning data and the imaging data. For instance, a reference anatomical feature identified from the positioning data may also be identified in the imaging data. In this regard, the imaging data may include three-dimensional imaging data. The imaging data may represent a three-dimensional model of the anatomy of a patient. Within this imaging data, a reference anatomical feature may be identified that correspond to the reference anatomical feature identified from the positioning data. In turn, the navigation module may use the commonly identified features from the imaging data and the positioning data to generate navigation data (e.g., including a position, orientation, and/or trajectory of the surgical instrument relative to the imaging data). This navigation data may be presented to a user as described in greater detail below.

It is contemplated that the surgical instrument and navigation assistance system contemplated herein may be used generally in relation to any surgical context. However, certain applications may have particular benefit in use of the navigation assistance system contemplated herein. For instance, surgeries involving sensitive and important anatomy may benefit from the use of navigation assistance. Examples include spinal surgery and neurosurgical applications. Moreover, other surgical contexts such as dental surgery and/or trauma surgery are contemplated. Further still, anatomy with delicate or precise positioning requirements may be particularly benefited from the concepts described herein such as in the context of surgical procedures involving the digits (i.e., fingers, toes) of a patient.

Further still, the form of the surgical instrument contemplated herein may generally be any configuration. However, in at least one preferred embodiment, the surgical instrument may comprise a pen-grip style instrument. In other applications (e.g., such as dental applications), the surgical instrument may comprise a right-angle instrument in which the tool portion extends perpendicularly to the major axis of the instrument gripped by the user. However, while such contexts may be described herein, it is to be understood that the present disclosure should not be limited to such specific recitations and can generally be applied to any surgical context and/or surgical instrument configuration.

As described above, the navigation module may be operative to generate navigation data in real time. In this regard, the navigation module may generate navigation data even during the operation of the surgical instrument relative to the patient. That is, the sensors may be disposed relative to the surgical instrument and patient to maintain an observable field even when the surgical instrument has engaged the patient in the operation. This may allow, for example, the sensors to continue to observe features as the surgical instrument (or a tool portion thereof) is advanced relative to the patient. That is, the sensors may continue to observe the position of the surgical instrument relative to the external features observed even as the tool portion is disposed internally to the patient. This may allow the navigation module to continue to generate navigation data that may include information regarding the position, orientation, and/or trajectory of the surgical instrument (and tool portion) relative to the imaging data.

While the navigation module may be operative to provide navigation data as described above, it may be beneficial to have additional or confirmatory information regarding the placement of the surgical instrument. Accordingly, the surgical instrument may also include a measurement system. For instance, the measurement system may be according to any one or more of U.S. Pat. No. 6,665,948 issued on Dec. 23, 2003 entitled "DRILL BIT PENETRATION MEASUREMENT SYSTEM AND METHOD," U.S. Pat. No. 9,358,016 issued on Jun. 7, 2016 entitled "DRILL WITH DEPTH MEASUREMENT SYSTEM," and/or U.S. patent application Ser. No. 15/336,202 published as U.S. Pub. No. 2017/0143440 filed on Oct. 27, 2017 entitled "TECHNIQUES AND INSTRUMENTS FOR PLACEMENT OF ORTHOPEDIC IMPLANTS RELATIVE TO BONE FEATURES," all of which are assigned to the present applicant and are incorporated by reference in their entirety.

In any regard, the measurement system may be operative to determine the position of a tool portion and/or implant relative to anatomic structures using, for instance, a depth sensor and a tool drive sensor such as a force sensor or the like. In turn, the measurement system may be used to provide additional information to the navigation module to supplement and/or confirm the position of the surgical instrument relative to the anatomy of the patient. For instance, the measurement system data may be more granular or specific in relation to placement of the surgical instrument relative to certain anatomy such as bones or the like. In turn, the measurement system data may supplement the navigation data to provide more detailed navigation data for use by the user.

The navigation data generated by the navigation module may be used in a number of different manners in various applications. For instance, the navigation data may be output for display to a user. The output may include a graphical or pictorial representation of the position of the surgical instrument relative to the patient. This may include superimposing the surgical instrument relative to the imaging data. As described above, the imaging data may be three-dimensional and the output may provide the surgical instrument in relation to the three-dimensional imaging data. The output may be provided on a display or the like that may be positioned near the patient for observation by the user during use of the surgical instrument. Alternatively, the navigation data may be presented in an augmented or virtual reality environment. For instance, the user may have a wearable display that the user looks through to view the patient. Navigation data may be presented on the display to augment the natural field of vision of the user. For instance, the imaging data or a portion thereof may be superimposed over the patient. Further still, navigation data may also be provided in the augmented reality display to assist the user in an operation using the surgical instrument.

In view of the foregoing, a first aspect includes a navigation assistance system for use with a surgical instrument. The system includes at least one sensor disposed relative to a patient on which an operation is to be performed. The sensor is operative to detect at least one reference anatomical feature of the patient adjacent to the surgical instrument to generate positioning data regarding a location of the surgical instrument relative to the reference anatomical feature. The system also includes a data repository comprising imaging data corresponding to an imaging study of the patient. The imaging data includes at least one imaged anatomical feature of the patient. The system also includes a navigation module that is operative to correlate the imaging data retrieved from the data repository with the positioning data to provide navigation data corresponding to the relative position of the surgical instrument with respect to the imaged anatomical feature of the patent for navigation assistance of the surgical instrument during the operation.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, in various embodiments one or more sensor arrangements may be provided. The at least one sensor may be disposed on the surgical instrument. Additionally or alternatively, a sensor may be positioned such that the surgical instrument and the patient are within the observation field of the sensor. That is, one or more wide-field sensors may be provided whose observation field extends to include the surgical instrument and the external anatomical feature of the patient. As will be described in greater detail below, such wide-field sensors may also be used to monitor additional components of the system such as a wearable display or may monitor the user of the system.

In an embodiment, in which the sensor is disposed on the surgical instrument (e.g., an "on-board" sensor), it may be appreciated that the sensor may be attached to the surgical instrument or integrated therewith. For instance, the sensor may be adapted to be retrofitted onto an existing surgical instrument such that the sensor engages or is otherwise disposed at the surgical instrument for monitoring the patient adjacent to the surgical instrument. Whether engaged or integrated with the surgical instrument, a plurality of sensors may be provided that may be disposed at the surgical instrument to have an observable field that extends in at least two directions relative to the surgical instrument. This may include a plurality of integrated sensors or may include a sensor array that is engageable with the surgical instrument. For instance, a collar or the like that extends about the surgical instrument may be provided that includes the plurality of sensors having fields of view that extend in different relative directions. In any regard, the plurality of sensors may define a collective observable field that extends substantially entirety about the surgical instrument. In this regard, one or more reference anatomical features may be observed in different directions relative to the surgical instrument to assist in generating the positioning data.

In an embodiment, the sensor may include a visual sensor and the positioning data may include visual data regarding the reference anatomical feature that comprises visible anatomy of the patient adjacent to the location of the surgical instrument. That is, the sensor may comprise a camera to generate imaging data or video data that is interpreted to observe an external, visible reference anatomical feature. The navigation module may include a machine vision system that may interpret the output of the visual sensor for identification of an external anatomical feature for assistance in generation of the positioning data.

The visual sensor may be supplemented with input from additional sensors such as any of the sensors described below. For instance, the visual sensor may be supplemented with a depth sensor to provide information regarding a contour of the skin of the patient adjacent to the surgical instrument for assistance in generating the positioning data. As such, the sensor may additionally or alternatively include at least one of an ultrasound sensor, a proximity sensor, an infrared sensor, a laser sensor, or a contact sensor. Further still, combinations of such sensors may be provided, potentially with overlapping or concurrent observation fields. In this regard, the external anatomical feature may be identified based on the input from a plurality of different sensors, potentially of different types.

The imaging data may include three-dimensional data. In this regard, the imaging data may comprise a three-dimensional model of the patient's anatomy. The imaging data may include internal anatomical features as well as external anatomical features. For instance, in the case of a three-dimensional model, the entirety of at least a portion of the patient's anatomy may be provided. The navigation module may be operative to selectively display or analyze portions of the imaging data (e.g., to include only a portion of the anatomical features contained in the imaging data). In this regard, the imaging data may also include information regarding relationships or relative orientations and positions of various anatomy of the patient. Such imaging data may be freely manipulated in a virtual space to allow for orientation (e.g., rotation, translation, or the like) in a virtual reference space. This may allow for manipulation of the imaging data to correlate or align the imaging data in relation to the positioning data.

Moreover, various different patient states may be imaged that correspond to different anatomic positions. For instance, a patient may be imaged with a leg, arm, foot, hand, fingers, and/or toes in various different configurations such that the imagining data may include all such configurations for comparison to the positioning data for correlation therewith. Moreover, as the imagining data may be represented as a virtual three-dimensional model, the imaging data may be digitally manipulated to provide the imaged anatomy of the patient in different configurations. That is, for example, a patient's leg may be digitally manipulated to represent a range of motion of the upper leg relative to the lower leg as articulated at the knee. Rather than imaging such articulation, the three-dimensional model of the patient's anatomy may be digitally manipulated to represent such articulation. In an application, the image study may include a computed tomography (CT) scan. In another application, the image study may include a magnetic resonance imaging (MRI) scan.

In an embodiment, the navigation module may be operative to correlate the reference anatomical feature of the patient from the positioning data to a corresponding reference anatomical feature appearing in the imaging data. Specifically, the navigation module may align the corresponding reference anatomical feature of the imaging data with the reference anatomical feature of the patient from the positioning data to align the imaging data relative to the position of the patient. The alignment of the corresponding reference anatomical features may include analysis of different configurations the imaging data (e.g., corresponding to different patient positions) or manipulation of the imaging data. This may be particularly relevant in the context of real time monitoring of the position of the surgical instrument in which a patient may move or change positions. In this regard, the sensor may detect such change in position of the patient relative to the surgical instrument. In order to maintain correlation or alignment of the imaging data to the sensed position of the patient, the imaging data may be analyzed or manipulated to maintain the correlation therebetween. As such, even in the event that a patient moves, the navigation data may be updated in real time.

In an embodiment, the navigation data may include a representation of the surgical instrument relative to the imaging data based on the correlated position of the surgical instrument relative to the reference anatomical feature. The representation of the surgical instrument may be displayed relative to the imaging data to allow a user to perceive the location of the surgical instrument relative to the anatomy of the patient. Moreover, even in instances where it is not necessary to represent the actual surgical instrument (e.g., in the case of an augmented reality display), a representation of the surgical instrument may include information such as a projected trajectory or the like based on the current location, orientation, and/or position of the surgical instrument relative to the patient. Moreover, the navigation data may include guidance information that may direct the user in relation to placement of the surgical instrument. For instance, the navigation may provide feedback and/or instructions regarding how the surgical instrument should be placed relative to the patient. Such placement may be monitored and confirmed through further feedback regarding placement.

In various embodiments, the reference anatomical feature may be any appropriate feature that may be sensed by the sensor to determine the relative position of the instrument relative to the reference anatomical feature. For instance, the reference anatomical feature may include a dimensionally stable structure (e.g., including a structure of bone, cartilage, or the like). In this regard, the reference anatomical feature may be an internal anatomical feature. For instance, the reference anatomical feature may be a bone. Additionally or alternatively, the reference anatomical feature may be an external anatomical feature. As described above, the reference anatomical feature may be any appropriate feature that may be observed from an external perspective relative to the patient. A specific example may include a contour of the skin of the patient. This may be particularly relevant in the case where the surgical instrument is positioned adjacent to the torso or abdomen of the patient in which other reference anatomical features may not be readily observable. In other contexts, the reference anatomical feature may include, but are not limited to, an arm, a leg, a hand, a foot, a finger, a toe, a head, a torso, a spine, a pelvis, or other dimensionally stable anatomical landmark such as the navel or the like, or combinations thereof. Furthermore, the imaged anatomical feature may include at least one subcutaneous structure. Examples include, but are not limited to, a bone, a blood vessel, a nerve, or combinations thereof.

The navigation data may be at least in part based on a known relative position between the sensor and the surgical instrument. That is, the orientation of the sensor relative to the surgical instrument may be known or detectable whether the sensor is integrated with the surgical instrument or provided separately.

In an embodiment, the navigation data may be displayed in relation to the imaging data. As described above, the navigation data and the imaging data may be displayed on a display (e.g., a monitor or the like) positioned near the patient. As such, the display may be observable by the user when the user has positioned the surgical instrument adjacent to the patient. In an embodiment, the navigation data may be displayed in an augmented reality display positioned relative to a user. For example, the user may wear a wearable display (e.g., smart glasses), a transparent display may be positioned between the user and the patient, or some other augmented reality display may be employed. In any regard, the navigation data may be displayed on the augmented reality display such that the navigation data may be superimposed on the actual patient when observed through the augmented reality display. The navigation data may also be displayed in relation to at least a portion of the imaging data. For instance, a user utilizing the augmented reality display may position the surgical instrument adjacent to the patient. The navigation module may generate the navigation data. In turn, the navigation data (e.g., a projected trajectory of the surgical instrument in its current position) may be superimposed relative to the patient when observed through the augmented reality display. Moreover, the navigation data (e.g., projected trajectory) may be presented in relation to one or more portions of the imaging data (e.g., internal anatomical structures such as blood vessels or nerves) that are also superimposed relative to the patient when observed through the augmented reality display. In turn, a user may view the patient through the augmented reality display and be able to observe, for example, a representation of internal anatomical structures such as bones, blood vessels, or nerves in relation to the trajectory of the surgical instrument as currently positioned. As may be appreciated, the navigation data may include trajectory information regarding the surgical instrument relative to the patient.

In an embodiment, the navigation data may be provided in real time relative to movements of the surgical instrument relative to the patient. Accordingly, the user may manipulate the surgical instrument to align the trajectory as desired relative to the internal anatomical structures as desired. In addition, the navigation data may be at least partially based on the position of the augmented reality display relative to the patient. For instance, the user may alter their vantage of the patient in which case the navigation data and/or imaging data presented to the user may be correspondingly updated to compensate for the change in position of the user. This may allow a user to observe the navigation data from multiple perspectives prior to initiating an operation with the surgical instrument.

In an embodiment, the system may also include a measurement system disposed at the surgical instrument that is operative to measure a displacement of a tool portion of the surgical instrument relative to a reference point to output a displacement signal and to measure a tool drive parameter that is characteristic of the tool portion acting on the patient to output a tool drive signal representative the tool drive parameter as the tool portion is advanced relative to anatomy of the patient. In turn, the navigation data may be at least in part based on the displacement signal and the tool drive signal. As described above, the displacement signal and the tool drive signal may be used to confirm a position of the surgical instrument relative to the anatomy of the patient or may be used to provide a more accurate determination of the position.

In an embodiment, an approximate estimated surgical instrument location is provided to the navigation module. The approximate estimated surgical instrument position may be provided in relation to the imaging data. Accordingly, the navigation module may be operative to reduce the imaging data to be analyzed to an area of interest comprising less than the entirety of the imaging data based on the approximate estimated surgical instrument position. For instance, the user may indicate that the surgical instrument is being positioned adjacent to the left leg of the patient. In turn, the navigation module may limit the imaging data analyzed to an area of interest with in the imaging data corresponding to the left leg of the patient. The approximate estimated surgical instrument position may be provided by the user through interface with a display or other appropriate user interface.

In addition or as an alternative to displaying the navigation data, the navigation data may include an alert based on at least one of a position of the surgical instrument relative to the internal anatomical feature of the patient or a trajectory of the surgical instrument relative to the internal anatomical feature of the patient. For instance, the navigation data may indicate that the surgical instrument is positioned such that a trajectory of the surgical instrument intersects an internal anatomical feature that is sensitive such as a nerve or blood vessel. In such a context, an alert may be provided to inform the user that such a condition exists. Alternatively, if the position of the surgical instrument nears a feature of interest or a feature that is sensitive, an alert may also be provided. In an application, operation of the surgical instrument may be at least in part based on the alert. In this regard, operation of the surgical instrument may be ceased at least in part based on the alert. In addition, as described above, the navigation data may include feedback or instructions regarding placement or movement of the surgical instrument. This may be combined with an alert such that a user may be provided with an alert and further feedback regarding how to place, move, or otherwise manipulate the surgical device in response to the alert.

A second aspect includes a navigation assistance system for use in a surgical operation. The navigation assistance system includes a surgical instrument comprising a tool portion. The system further includes a measurement system disposed at the surgical instrument that is operative to measure a displacement of the tool portion of the surgical instrument relative to a reference point to output a displacement signal and to measure a tool drive parameter that is characteristic of the tool portion acting on the patient to output a tool drive signal representative the tool drive parameter as the tool portion is advanced relative to anatomy of the patient. The system includes at least one sensor disposed on the surgical instrument that is operative to detect at least one reference anatomical feature of the patient adjacent to the surgical instrument to generate positioning data regarding a location of the surgical instrument relative to the reference anatomic feature. Furthermore, the system includes a data repository comprising imaging data corresponding to an imaging study of the patient. The imaging data includes at least one imaged anatomical feature of the patient. In turn, the system includes a navigation module that is operative to correlate the imaging data retrieved from the data repository with the positioning data to provide navigation data. The navigation data is at least in part based on the displacement signal and the tool drive signal and corresponds to the relative position of the surgical instrument with respect to the imaged anatomical feature of the patient for navigation assistance of the surgical instrument during the operation.

A number of feature refinements and additional features are applicable to the second aspect. These feature refinements and additional features may be used individually or in any combination. As such, each of the foregoing features discussed in relation to the first aspect may be, but are not required to be, used with any other feature or combination of features in connection with the second aspect.

A third aspect includes a method of providing navigation assistance data for use in a surgical operation. The method includes obtaining positioning data comprising a relative position of a surgical instrument relative to at least one reference anatomical feature of a patient adjacent to a location of the surgical instrument using at least one sensor disposed relative to the patient and retrieving imaging data corresponding to an imaging study of the patient from a data repository. The imaging data includes patient anatomy including at least one imaged anatomical feature of the patient. In turn, the method includes correlating the imaging data retrieved from the data repository with the positioning data from the sensor to generate navigation data corresponding to the relative position of the surgical instrument with respect to the imaged anatomical feature of the patent for navigation assistance of the surgical instrument during the operation.

A number of feature refinements and additional features are applicable to the third aspect. These feature refinements and additional features may be used individually or in any combination. As such, each of the foregoing features discussed in relation to the first aspect may be, but are not required to be, used with any other feature or combination of features in connection with the third aspect.

BRIEF DESCRIPTION OF THE DRAWINGS

FIGS. 7A-7H depict various embodiments illustrating use of a surgical instrument according to the present disclosure including potential displays for presentation of information to a user.

DETAILED DESCRIPTION

Figure 1:
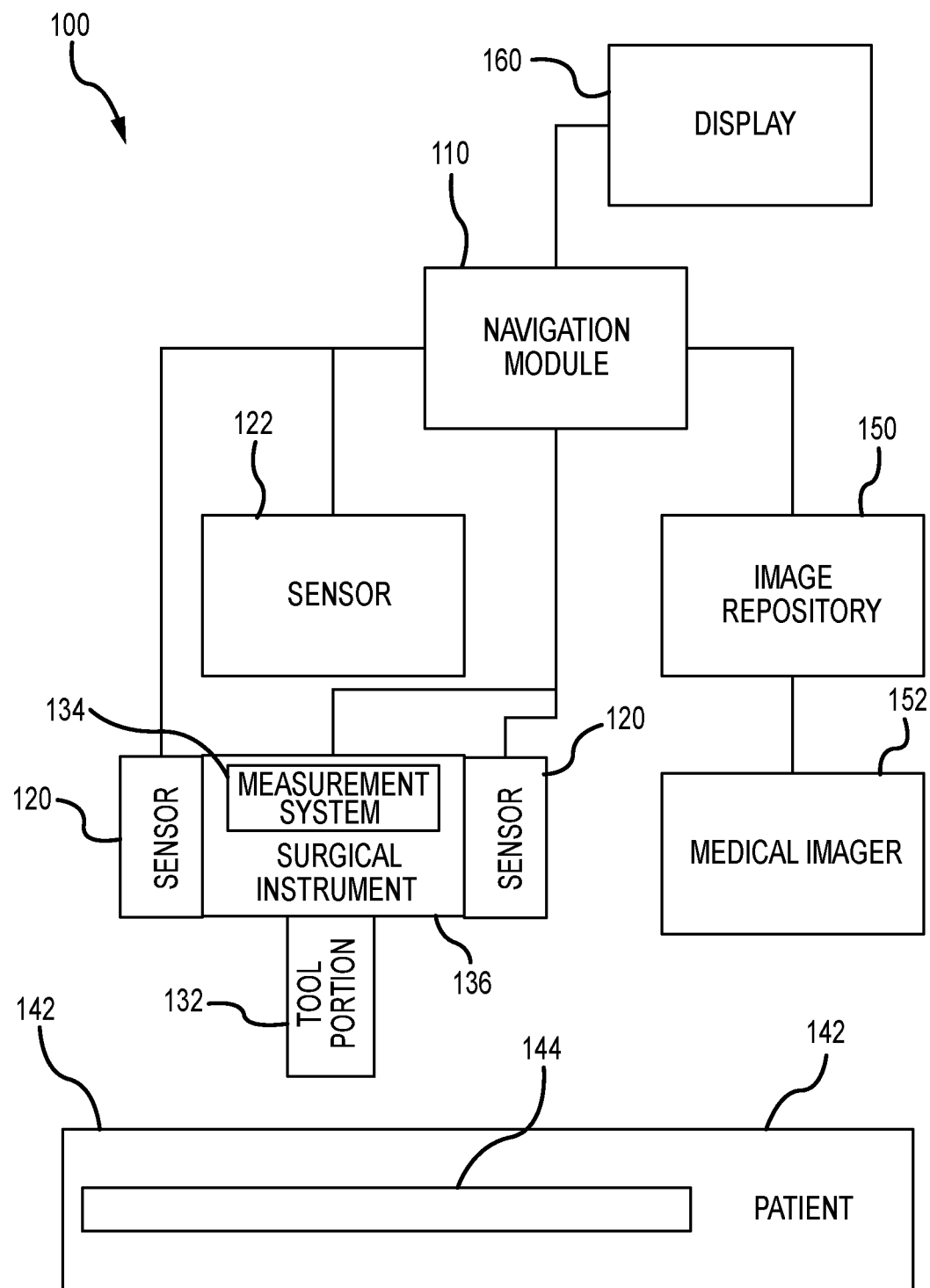
FIG. 1 depicts an embodiment of a navigation assistance system that may be used to provide navigation data to a user regarding relative location and/or trajectory of a surgical instrument with respect to a patient.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

FIG. 1 depicts a schematic representation of an embodiment of a system 100 that may be used as described herein to provide navigation data in connection with the use of a surgical instrument 100 to perform an operation on a patient 140. The system 100 may include a navigation module 110. The navigation module 110 may be in operative communication with one or more on-board sensors 120 and/or one or more wide-field sensors 122. As will be described in greater detail below the on-board sensors 120 and/or wide-field sensors 122 may be operative to detect a reference anatomical feature 142 of the patient 140. It may be appreciated that one or more on-board sensors 120 may be used in the absence of wide-field sensors 122, one or more wide-field sensors 120 may be used in the absence of on-board sensors 120, or a combination of one or more wide-field sensors 120 and one or more on-board sensors 122 may be used. Based on the detected reference anatomical feature 142, positioning data may be generated that describes the relative position between a surgical instrument 130 and a patient 140.

The navigation module 110 may comprise any appropriate hardware or software components to perform as recited herein. In this regard, the navigation module 110 may include one or more hardware components including, for example, a field programmable gate array, an application specific integrated circuit, or other hardware component. Additionally or alternatively, the navigation module 110 may be implemented using software. As such, reference to the navigation module 110 may include corresponding computer hardware for execution of the module including one or more processors that may be in operative communication with a physical memory device. Specifically, the one or more processors may retrieve instructions comprising non-transitory machine readable instructions that may be stored digitally on the physical memory device. In turn, the instructions, when executed by the processor, may configure the processor to perform the functionality described herein. Additional computer hardware may be provided to facilitate operation of the processor including busses, networking components, or the like, and may be included as part of the navigation module 110.

The navigation module 110 may also be in operative communication with an image repository 150. The image repository 150 may include a physical memory device that may be operative to store imaging data digitally on the physical memory device. Specifically, the image repository 150 may include imaging data that may be obtained by way of an imaging study conducted using a medical imager 152 that may be operative to image the patient 140. As referenced above, the medical imager 152 may comprise hardware corresponding to any appropriate medical imaging technology including, but not limited to, x-ray, magnetic resonance imaging (MRI), computer tomography (CT), positron emission tomography (PET), or any other appropriate medical imaging technology. The medical imager 152 may provide digital imaging data regarding the patient 140 resulting from an imaging study directly to the image repository 150. Alternatively, the imaging data may be digitized for storage in the image repository 152. Further still, the imaging data may be transferred from the imager 152 to the image repository 152 using any appropriate means.

The navigation module 110 may also be in operative communication with the display 160. The display 160 may present the navigation data generated by the navigation module 110 to a user of the system 100. As will be described in greater detail below, the display 160 may include any one or more of a variety of display technologies that may allow a user to perceive the navigation data as generated by the navigation module 110.

The navigation module 110 may also be in operative communication with the surgical instrument 130. The surgical instrument 130 may have a tool portion 132 that acts upon the patient 140 during the operation of the surgical instrument 130. The surgical instrument may be, but is not limited to, a drill, saw, ream, grinder, or another surgical tool. In this regard, the tool portion may comprise a drill bit, a reamer, a grinding tool, or other appropriate tool.

The surgical instrument 130 may also include a measurement system 134 such as those described above. As may be appreciated, the surgical instrument 130 may include on-board sensors 120 such that the sensors 120 may be disposed at or integrated with the surgical instrument 130. In this regard, bi-directional communication may be established between the navigation module 110 and the instrument 130. As such, data from the instrument 130 may be provided to the navigation module 110 such as outputs from the sensors 120 and/or measurement system 134. Further still, the navigation module 130 may provide data to the instrument 130 (e.g., including a control signal that controls operation of the surgical instrument 130 as described above).

As described above and shown schematically in FIG. 1, the patient 140 may present reference anatomical features 142 (e.g., that may comprise external or visible anatomical features). In addition, the patient may have internal anatomical features 144 which may appear in the imaging data. Such internal anatomical features may be alternatively referred to as imaged anatomical features. The reference anatomical features 142 may be visible from an exterior the patient 140. In contrast, the internal anatomical features 144 may not be visible from an exterior of the patient 140. However, the medical imager 152 may be operative to image the patient 140 in an imaging study such that both reference anatomical features 142 as well as imaged anatomical features 144 are included the imaging data stored in the image repository 150. The imaging data may be generated by the medical imager 152 in real time to provide real time imaging data regarding the patient 140. Alternatively, the medial imager 152 may image the patient 140 prior to use of the instrument 140 such that the imaging data regarding the patient 140 from a previously conducted imaging study may be stored in the image repository 152. As described above, the imaging data from the previously conducted imaging study may include imaging data corresponding to the patient in a number of configurations having the patient in various physical positions. In addition, the imaging data may include or be analyzed to produce imaging data corresponding to digital manipulations of the imaging data to result in different configurations of the patient anatomy.

In some embodiments, a wide-field sensor 122 may be provided separate from the surgical instrument 130. The wide-field sensor 122 may include within its field of observation both the medical instrument 130 and the patient 140. In this regard, the wide-field sensor 122 may observe the surgical instrument 130 in relation to one or more reference anatomical features 142. This may be used to generate positioning data that is provided to the navigation module 110 for generation of navigation data as will be described in greater detail below.

Figure 2:
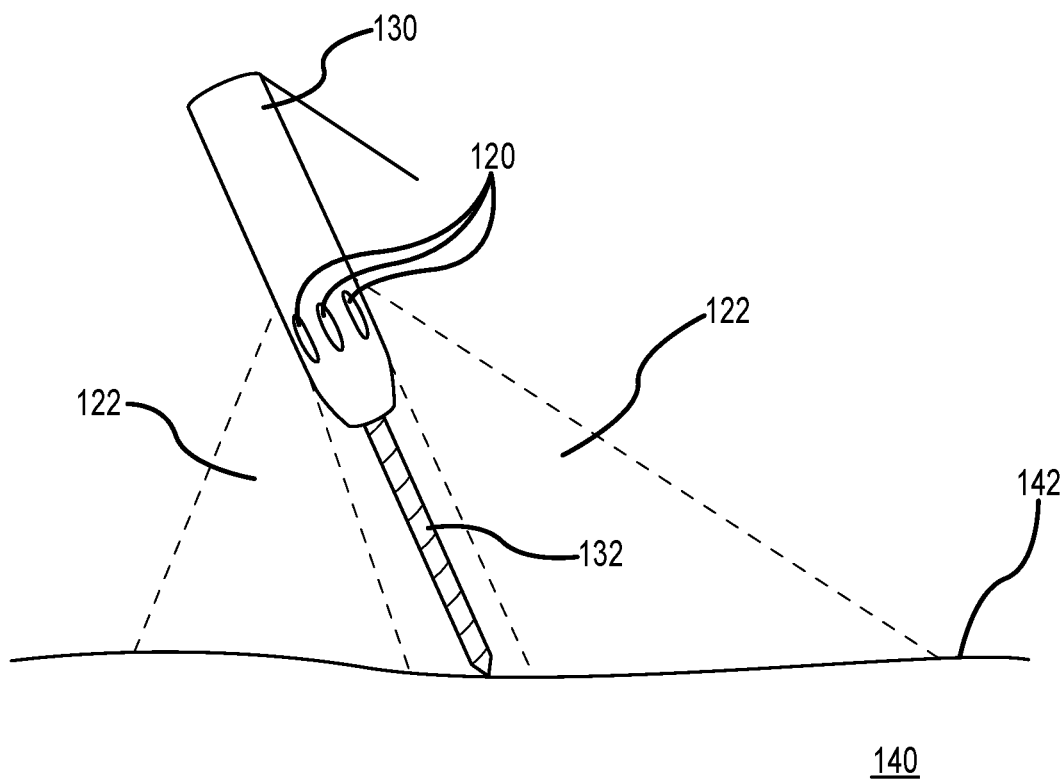
FIG. 2 depicts an embodiment of a powered surgical instrument disposed relative to a patient with sensors for obtaining data regarding the position of the surgical instrument relative to the patient.

Additionally or alternatively, the surgical instrument 130 may include on-board sensors 120 that are provided at or integrated with the instrument 130. With further reference to FIG. 2, one such surgical instrument 130 that includes integrated sensors 120 is shown. The surgical instrument 130 has been disposed relative to the patient 140. As can be seen, the tool portion 132 may be in contact with an reference anatomical feature 142 of the patient 140. In this regard, the on-board sensors 120 may define a field of observation 122 that may capture the reference anatomical features 142. As described above, the reference anatomical features 142 may correspond to appendages such as arms, legs, hands, feet, fingers, toes; a portion of the body such as a torso, head, pelvis; or may correspond to contours of the skin of the patient 140 to provide the positioning data that relates the relative position of the surgical instrument 130 to the reference anatomical features 142 observed by the sensors 120.

A number of potential sensors and sensor configurations are contemplated as potentially applicable in various embodiments of the present disclosure. For instance, the sensors 120 and/or sensors 122 may include ultrasonic, infrared, laser, and/or optical sensors. A number of potential technologies for interpreting sensor inputs may be provided without limitation. For instance, a time-of-flight sensor may be employed as any one of an ultrasonic, infrared, laser, or optical sensor. Moreover, in relation to optical sensors, the sensors may include stereo-optic sensors, time-of-flight sensors, structure light sensors, and/or light field sensors. In connection with any of the foregoing sensors, the surgical instrument may include appropriate emitters and receptors for use in connection with any of the sensors described herein, as will be described in greater detail below. Additionally, it is contemplated that the sensors 120 and/or sensors 122 may include inertial measurement sensors and/or mechanical sensors (e.g., including an articulated arm).

In this regard, specific combinations of the foregoing sensors have been contemplated. Accordingly, certain combinations of sensors are to be described herein, yet it should be understood such descriptions are not to be limiting and other combinations not specifically addressed herein are contemplated. Moreover, description of a sensor configuration as comprising a combination of sensor types is intended to confer a specific combination of sensor technologies without necessarily imply a quantity of sensors uses. As such, description of a sensor configuration as including an optic sensor and an ultrasound sensor does not necessarily limit such a configuration to a single optic sensor and a single ultrasound sensor.

In an embodiment, the sensor configuration may include a multi-imager optical sensor array. In this embodiment, a plurality of sensors (e.g., three or more optical sensors) may be arrayed to observe the surgical site. In turn, the imaging data obtained by the optical sensor array may be provided to a controller that stitches the images together to create depth and/or orientation information.

In another embodiment, the sensor configuration may include a three-dimensional imager and infrared time-of-flight sensor. This may include a single imager with an infrared light source and a time of flight controller hardware. This approach may utilize infrared wavelength input of an imager to measure the time of flight of infrared light from the emitter to determine image field depth and to capture a surgical site image.

In another embodiment, the sensor configuration may include a structured light imager. This approach may include a single imager plus a micromirror array controller. This may include use of a micromirror array (e.g., utilizing digital light processing technology) to create depth information for an image.

In another embodiment, the sensor configuration may include a light field (plenoptic) lens and imager. This approach may employ a single imager that utilizes a special light field lens called a plenoptic lens that captures information about the light field emanating from a scene including the intensity of light in a scene and the direction that the light rays are traveling in space. In turn, software may process the captured light field information to create a three-dimensional image.

In another embodiment, the sensor configuration may include an imager and articulating arm. In this approach, the interment may be engaged with an articulating arm that may measure the position and/or orientation of the instrument in the field. This may be coupled with an imager to capture information regarding the surgical site.

In still another embodiment, the sensor configuration may include an imager, an inertial measurement unit, and a laser time of flight sensor. In this approach, the inertial measurement unit may measure the orientation of the drill and may utilize the laser time of flight sensor to determine the depth of the instrument relative to the patient.

In another embodiment, the sensor configuration may include an imager, an inertial measurement unit, and a laser time of flight sensor. In this approach, a single imager may be provided in combination with an inertial measurement unit to generate orientation information regarding the instrument. Additionally, a time of flight infrared sensor may provide a depth measurement of the instrument relative to the patient. This may utilize an image to locate the surgical site and then uses the inertial measurement unit data to orient the instrument.

In an embodiment, the sensor configuration may include an imager, an inertial measurement unit, and an ultrasound sensor. In this approach, a single imager may be provided in combination with an inertial measurement unit to generate orientation information regarding the instrument. Additionally, an ultrasound sensor may provide a depth measurement of the instrument relative to the patient. This may utilize an image to locate the surgical site and then uses the inertial measurement unit data to orient the instrument.

In yet another embodiment, the sensor configuration may include a multi-imager optic sensor and an infrared time of flight sensor. In this embodiment, a plurality of sensors (e.g., three or more optical sensors) may be arrayed to observe the surgical site. In turn, the imaging data obtained by the optical sensor array may be provided to a controller that stitches the images together to create depth and/or orientation information. Additionally, the time of flight infrared sensor may be utilized to determine a depth of the instrument relative to a starting datum.

Accordingly, the navigation module 110 may be operative to retrieve imaging data from the image repository 150. The navigation module 110 may be operative to identify a corresponding reference feature from the imaging data corresponding to the reference anatomical features 142 of the positioning data generated by the sensors 120. In turn, the imaging data may be correlated to the positioning data. As such, the navigation data generated by the navigation module 110 may describe the position of the surgical instrument 130 relative to the imaging data including imaged anatomical features 144.

Figure 3:
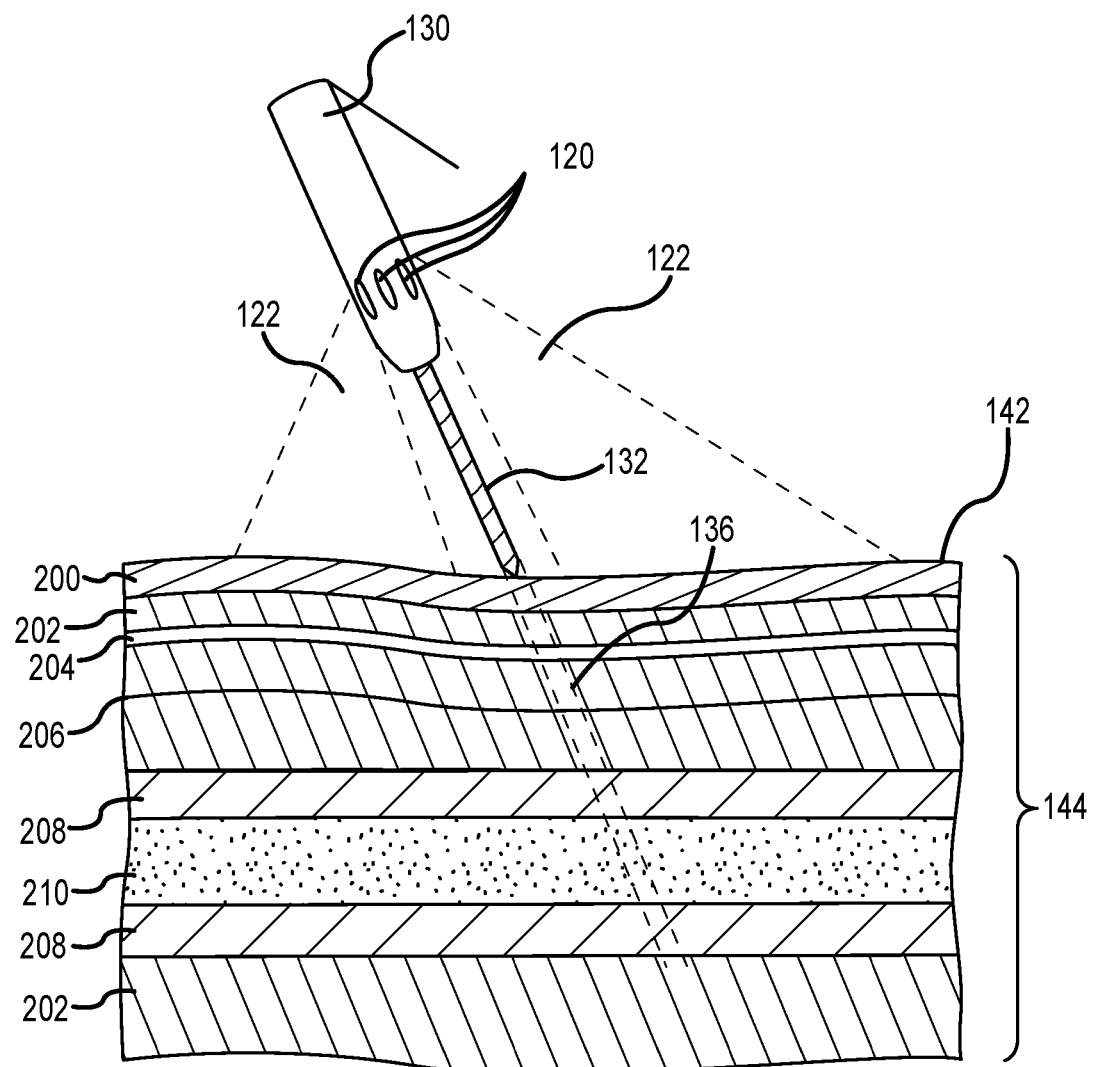
FIG. 3 depicts an embodiment of a correlation of imaging data from an imaging study with a position of a surgical instrument determined by sensors on the surgical instrument to provide navigation data regarding the position and trajectory of the surgical instrument relative to non-visible anatomical features from the imaging data.

In this regard, FIG. 3 may illustrate one example of navigation data that may be displayed on the display 160 where the internal anatomical features 144 are provided from the imaging data such that the position of the surgical instrument 130 relative to the imaged anatomical features 144 may be shown.

As way of illustration, the internal anatomical features 144 may include a number of different structures. For example, the skin layer 200 may be represented in the imaging data corresponding to the imaged anatomical features 144. Moreover, muscle tissue 202 may be represented. Further still, features such as blood vessels 204 and/or nerves 206 may also be represented in the imaging data and correspond to imaged anatomical features 144. A bone of the patient 140 may be represented in the imaged anatomical features 144. Specifically, a hard outer cortex 208 of a bone may represented as well as an inner medullary layer 210. While a number of anatomical features have been illustrated in FIG. 3 is relating to internal or imaged anatomical features 144, it may be appreciated that any variety of other imaged anatomical features 144 capable of being imaged and included in the imaging data may be provided without limitation.

FIG. 3 also illustrates that a trajectory 136 of the surgical instrument 130 may be provided in the navigation data. The trajectory 136 may correspond to a projected trajectory of the surgical instrument 130 (e.g., the tool portion 132) if the surgical instrument 130 were to be advanced along a working axis of the surgical instrument 130. For instance, the working axis may correspond to the axis of rotation for a rotary tool such as a drill or the like. In any regard, the trajectory 136 may be presented in relation to the imaged anatomical features 144 of the imaging data. As may be appreciated, this trajectory 136 may be provided to the user even prior to the surgical instrument 130 initiating the operation using the surgical instrument 130. In this regard, a user may be operative to modify the position of the surgical instrument 130 to modify the corresponding trajectory 136 (e.g., to avoid certain internal anatomical features 144). Furthermore, while FIG. 3 represents the navigation data relative to the imaged anatomical features 144 as two-dimensional, it may be appreciated that the navigation and/or imaging data may include three-dimensional data such that the position, orientation, and/or trajectory 136 of the surgical instrument 130 relative to the imaged anatomical features 144 may be presented in three-dimensions.

Another representation of a potential display 160 is shown in FIG. 7A, FIG. 7C, FIG. 7E, FIG. 7F, and FIG. 7G. In FIG. 7A, a depiction of the anatomy 164 of the patient to be operated on is shown. In addition, a trajectory 136 of an instrument is depicted. Furthermore, an acceptable trajectory range 162 is shown. In this regard, as shown in FIG. 7F, if the trajectory 136 were to be determined to be outside the acceptable trajectory range 162, an alarm 166 may be presented on the display 160. In addition, operation of the instrument may be terminated. In FIG. 7G, a display 160 configuration is shown in which the trajectory 136 is within the acceptable trajectory range 162 such that an indication 168 of proper operation is provided. As shown in FIG. 7C and FIG. 7E, the display 160 may be positioned within the field of view of a surgeon during an operation.

The navigation data generated by the navigation module 110 may be presented to a user in any appropriate manner. For example, the display 160 may be positioned near the patient 140 to present navigation data to the user who is positioning the surgical instrument 130 adjacent to the patient 140. As described above, the position of the surgical instrument 130 relative to the patient 140 may be obtained in relatively real time (e.g., with a delay that does not impact surgical operations such as less than about a second or so)

such that the manipulation of the surgical instrument 130 relative to the patient 140 may be reflected in the navigation data presented to the user on the display 160 in corresponding real time. The display 160 may be any appropriate display that may include monitors or the like positioned near the patient 140.

In an alternative embodiment, the display 160 may correspond to an augmented reality display 170 that may include projection of images within the field of view of the user. One such embodiment is shown in FIG. 7D. This may include a projector portion 172 projection of images onto a transparent medium 174 that allows a user to look through the transparent medium 174. In this regard, images may be superimposed over objects in the field of the view of the user through the transparent medium 174. For instance, a number of wearable displays have been proposed that project images into the field of view of a user wearing glasses, a visor, or the like as shown in FIG. 7D. In this regard, the navigation data may be presented to the user wearing such a wearable display such that the navigation data may be presented to the user in relation to the field of view of the user. That is, navigation data may be displayed on the wearable display such that the navigation data is superimposed over the user's view of the surgical area such that the positioning of the surgical instrument 130 within the user's field of view allows for presentation of navigation data that potentially includes the position and/or trajectory of the surgical instrument 130 relative to imaged anatomical features 144 as represented by the imaging data projected into the user's field of view to be superimposed over corresponding portions of the patient 140. The augmented reality display may thus present navigation data and imaging data. The imagining data may allow the user to visualize non-visible imaged anatomical features 142, which may be superimposed on the user's view of the patient 140. In addition, the imaging data may be presented even when the operation has commenced. This may include superimposing imaging data in relation to areas disturbed or removed during the operation. As may be appreciated, in order to compensate for the changing orientation of the user wearing such a wearable display, the wearable display itself may include or be detected by sensors that may determine the position of the wearable display. This may allow the navigation data to be accurately projected onto the wearable display and reflect the position of the surgical instrument 130 and/or reference anatomical features 142 in relation to the navigation data.

Figure 4:
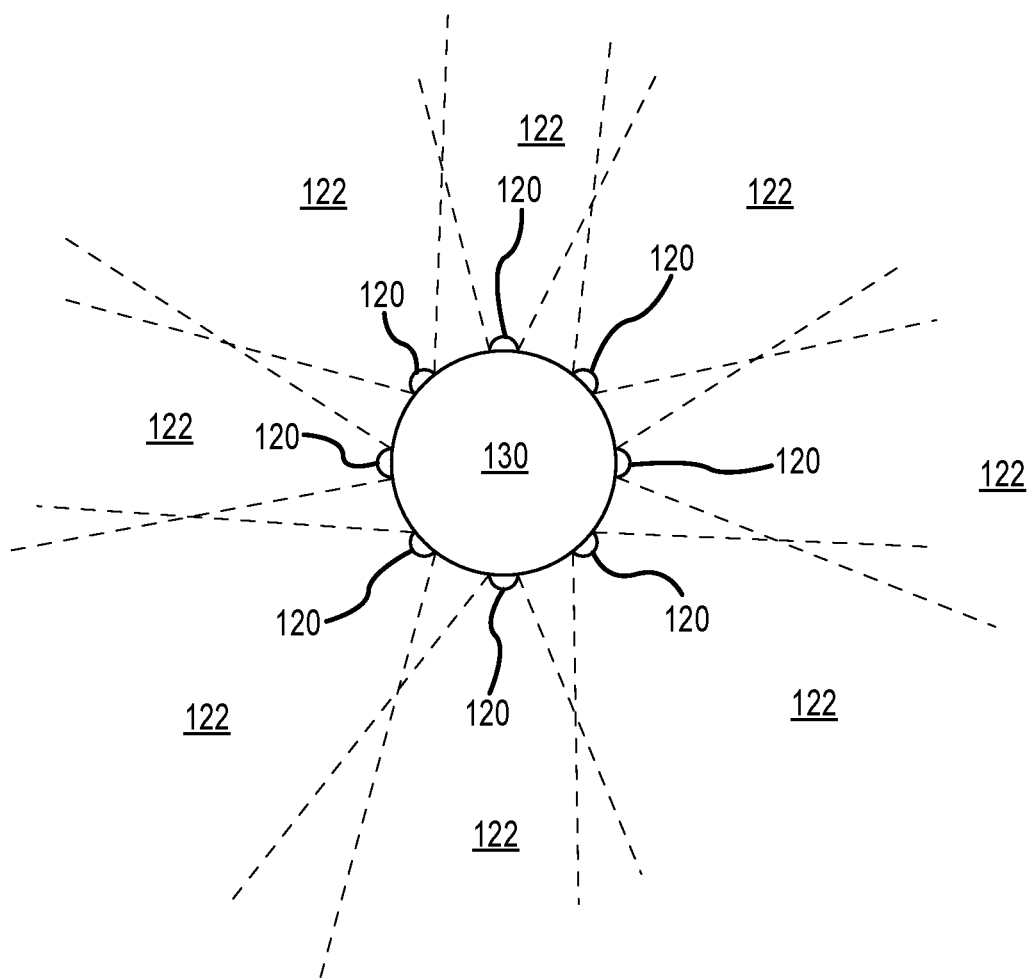
FIG. 4 depicts a top view of an embodiment of surgical instrument showing the field of observation of a number of sensors disposed relative to the surgical instrument.

Turning to FIG. 4, an embodiment of a surgical instrument 130 is depicted that includes a plurality of sensors 120. FIG. 4 represents an end view of the instrument 130 from either the top or bottom perspective. As may be appreciated each of the sensors 120 may have a corresponding observation field 122 extending from each respective sensor 120. As can be appreciated from FIG. 4, the observational fields 122 of the sensors 120 may be overlapping such that the collective field of view of the sensors 120 may extend about substantially all of the surgical instrument 130. In this regard, the sensors 120 disposed at the surgical instrument 130 may have a broad field of observation the may allow for identification of a number of reference anatomical features 142 for use in generating the positional data used for determining the position of the surgical instrument 130 relative to the reference anatomical features 142. This may be particularly useful in situations where the available reference anatomical features 142 are relatively vague, thus presenting difficulty in determining the location of the surgical instrument 130 for correlation to the imaging data. Examples may include portions of the torso or abdomen in which the contour of the patient's skin may be relied upon as the reference anatomical features 142 to be identified.

As briefly described above, the on-board sensors 120 and/or wide-field sensor 122 may comprise one or more of any appropriate type of sensor the may be used to identify reference anatomical features 142. For example, the on-board sensors 120 and/or wide-field sensors 122 may comprise optical sensors that obtain imaging data for use in identification of the reference anatomical features 142 adjacent to the surgical instrument 130. Further still, proximity sensors, laser sensors, or any other appropriate type of sensor that may be operative to observe and/or identify reference anatomical features 142 may be utilized. Moreover, combinations of different kinds of sensors may be provided without limitation. As may be appreciated, the observed reference anatomical feature 142 may simply correspond to a curvature or contour of the skin of the patient adjacent to the surgical instrument 130.

Figure 5:
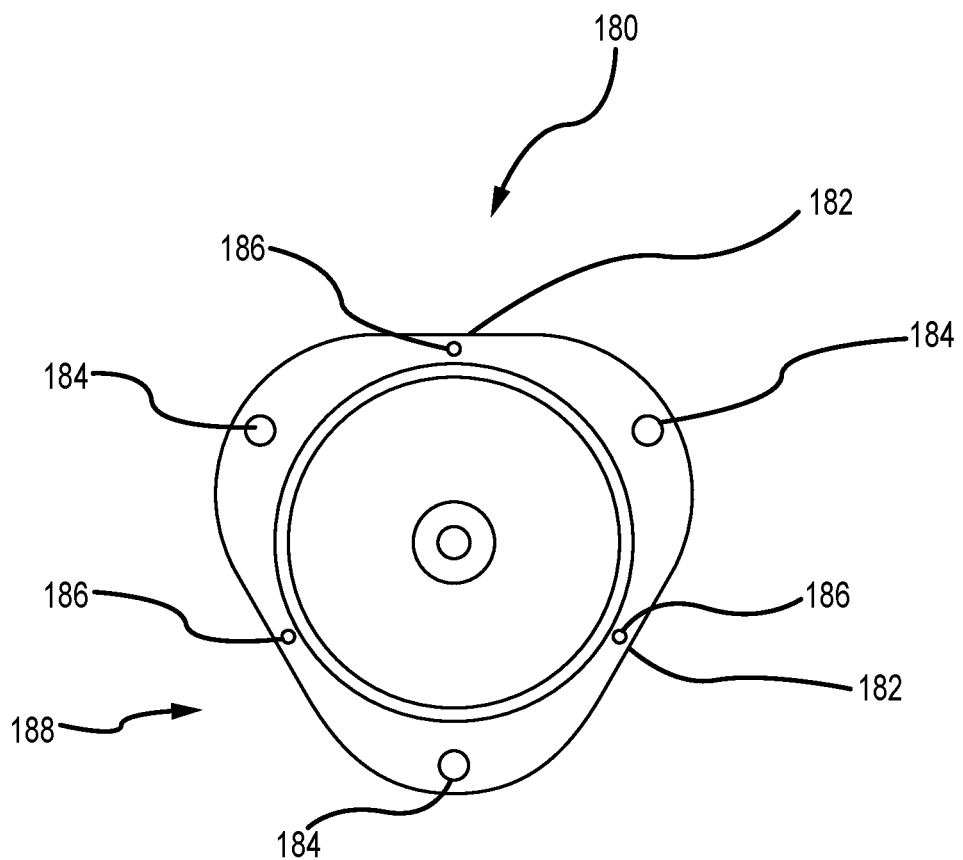
FIG. 5 depicts a front view of an embodiment of a surgical instrument showing an embodiment of a sensor configuration thereof.
Figure 6:
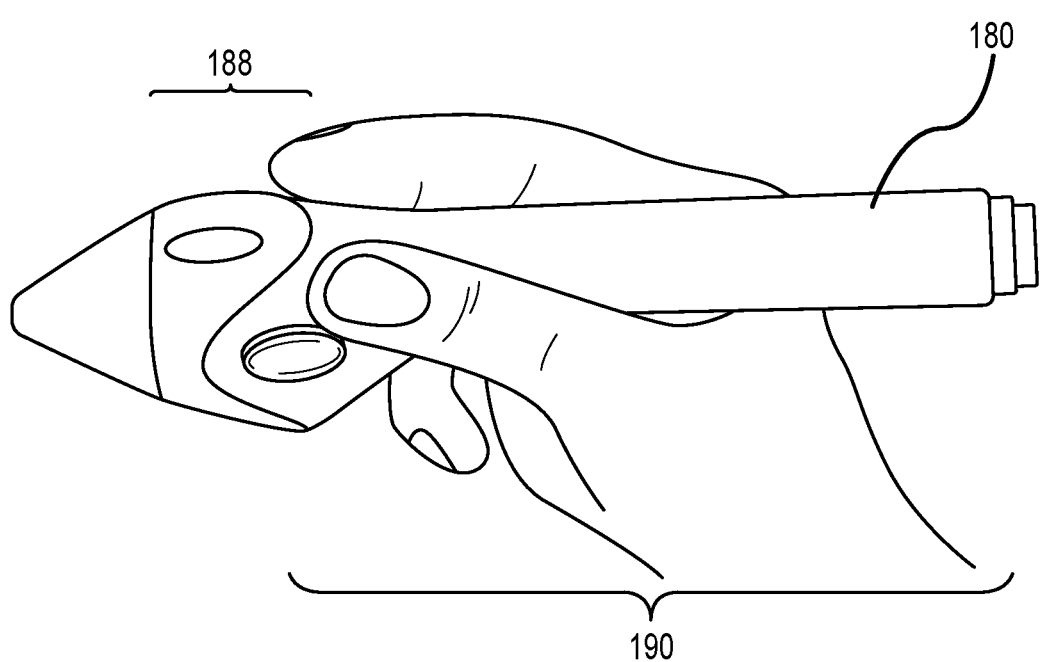
FIG. 6 depicts a side view of an embodiment of a pen-grip style instrument.

Another embodiment of an instrument 180 is shown in FIG. 5 and FIG. 6. This may comprise a pen-grip style instrument with a sensor portion 188 and a grip portion 190. The grip portion 190 may allow a user's fingers to be disposed relative to one or more triggers 182. The triggers 182 may facilitate interaction with the instrument 180 (e.g., to initiate operation, toggle selections, or any other appropriate action). Also in the sensor portion 188 may be a plurality of emitters 184 and cameras 186. In this regard, the instrument 180 may comprise a multi-imager optic sensor as described above. In addition, while not shown, the instrument 180 may also include an inertial measurement unit and/or an infrared time of flight sensor.

Figure 8:
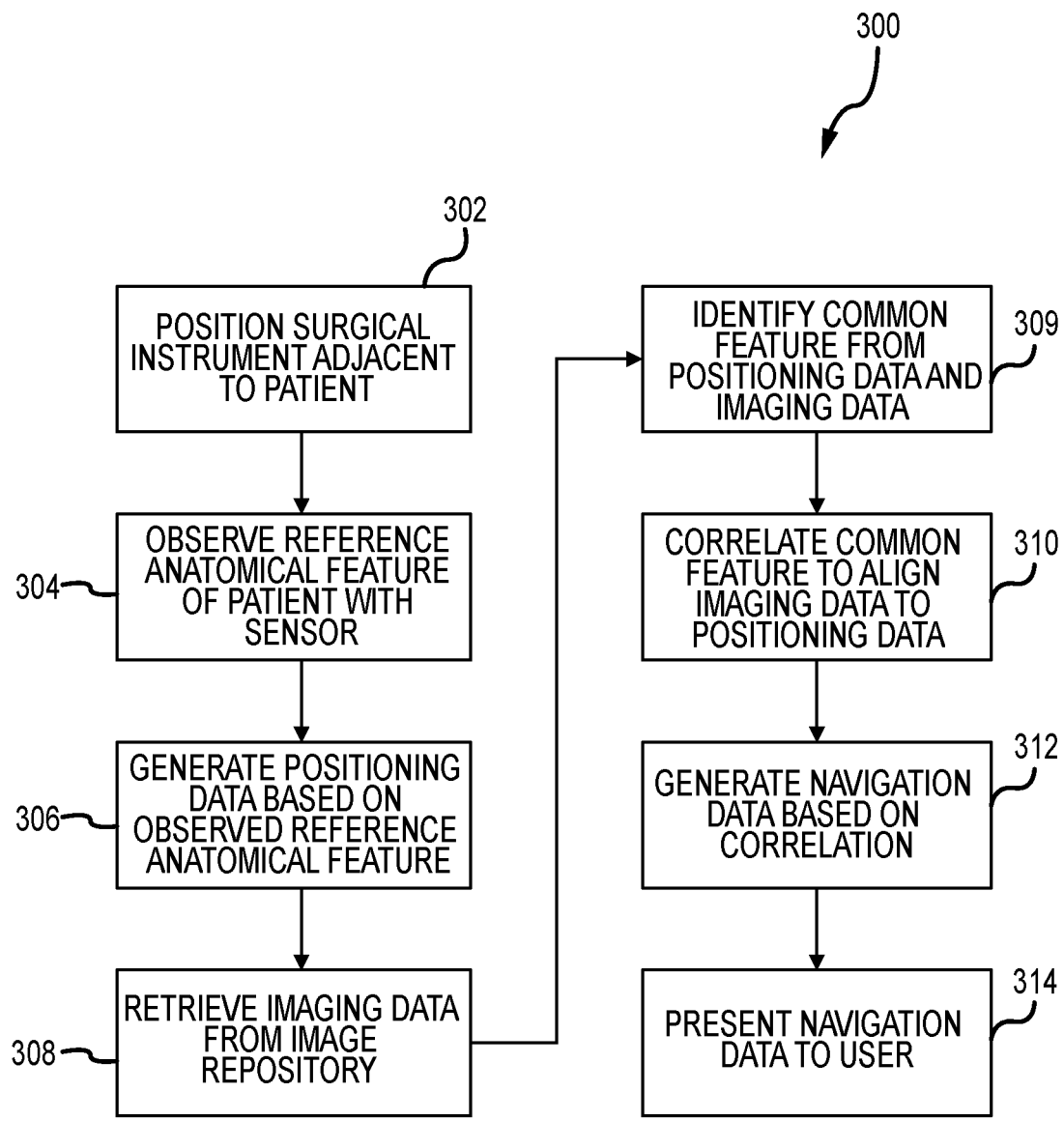
FIG. 8 depicts an embodiment of a method for generation of navigation data for use in connection with a surgical instrument.

With further reference to FIG. 8, a method 300 for generation of navigation data is depicted. The method 300 may include positioning 302 a surgical instrument adjacent to a patient. The method 300 may also include observing 304 reference anatomical features of the patient. This observing 304 may include use of on-boards sensors and/or wide-field sensors. In turn, the method 300 may include generating 306 positioning data regarding the relative position of the surgical instrument relative to the reference anatomical features.

The method 300 may also include retrieving 308 imaging data from an image repository. The method 300 also may include identifying 308 common reference features from the positioning data and the imaging data. For instance, the reference anatomical features observed 304 by the sensors may be provided in both the positioning data and the imaging data. Also as described above, the identifying 308 may include manipulation of the imaging data or analysis of different portions of imaging data to identify the common features or feature portions.

The method 300 may also include correlating 310 the common features to align the imaging data to the positioning data. The correlating 310 may include manipulating the imaging data in a virtual reference space to align the imaging data to the positioning data. In any regard, upon the correlating 310, the positioning data including information about the location of the surgical instrument may be related to the imaging data. Accordingly, the method 300 may include generating 312 navigation data based on this known relation between the surgical instrument and the features described in the imaging data. Further still, the method 300 may include presenting 314 the navigation data to a user of the system (e.g., in any of the manners described above).

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A navigation assistance system for use with a surgical instrument, comprising:
    a plurality of three-dimensional imaging sensors comprising time of flight sensors located on the surgical instrument and disposed relative to a patient on which an operation is to be performed, wherein the plurality of three-dimensional imaging sensors are operative to continually detect at least one reference anatomical feature of the patient in a surgical site adjacent to the surgical instrument to generate positioning data comprising a three-dimensional representation of the surgical site adjacent to the surgical instrument in a virtual reference space representing a location of the surgical instrument relative to the at least one reference anatomical feature, the positioning data comprising the three-dimensional representation of the at least one reference anatomical feature that comprises visible anatomy of the patient relative to the location of the surgical instrument, wherein the plurality of three-dimensional sensors are disposed on the surgical instrument to have an observable field of the patient at the surgical site that extends in at least two directions relative to the surgical instrument;
    a data repository comprising imaging data corresponding to an imaging study of the patient, wherein the imaging data includes at least one imaged anatomical feature of the patient; and
    a navigation module that is operative to continually correlate the imaging data retrieved from the data repository with the positioning data to align the three-dimensional representation of the at least one reference anatomical feature to the at least one imaged anatomical feature in the virtual reference space and continually provide navigation data corresponding to a relative position of the surgical instrument with respect to the at least one imaged anatomical feature of the patient for navigation assistance of the surgical instrument in real-time during the operation.

2. The navigation assistance system according to claim 1, wherein the plurality of sensors comprise a collective observable field that extends entirety about the surgical instrument.

3. The navigation assistance system according to claim 1, wherein the plurality of sensors further comprise at least one of an ultrasound sensor, a proximity sensor, an infrared sensor, a laser sensor, or a contact sensor.

4. The navigation assistance system according to claim 1, wherein the imaging data comprises three-dimensional data.

5. The navigation assistance system according to claim 4, wherein the imaging study comprises a computed tomography (CT) scan.

6. The navigation assistance system according to claim 4, wherein the imaging study comprises a magnetic resonance imaging (MM) scan.

7. The navigation assistance system according to claim 1, wherein the at least one reference anatomical feature comprises a dimensionally stable structure.

8. The navigation assistance system according to claim 7, wherein the at least one reference anatomical feature comprises an internal anatomical feature.

9. The navigation assistance system according to claim 8, wherein the at least one reference anatomical feature comprises a bone.

10. The navigation assistance system of claim 1, wherein the at least one reference anatomical feature comprises an external anatomical feature.

11. The navigation assistance system according to claim 10, wherein the at least one reference anatomical feature comprises a contour of skin of the patient.

12. The navigation assistance system according to claim 1, wherein the at least one reference anatomical feature comprises one or more of an arm, a leg, a hand, a foot, a finger, a toe, a head, a torso, a spine, a pelvis, or other dimensionally stable anatomical landmark detectable by at least one of the plurality of sensors.

13. The navigation assistance system according to claim 1, wherein the at least one imaged anatomical feature comprises at least one subcutaneous structure.

14. The navigation assistance system according to claim 13, wherein the at least one imaged anatomical feature comprises at least one of a bone, a blood vessel, or a nerve.

15. The navigation assistance system according to claim 1, wherein the navigation module comprises a machine vision system.

16. The navigation assistance system according to claim 1, wherein the navigation data is at least in part based on a known relative position between at least one of the plurality of sensors and the surgical instrument.

17. The navigation assistance system according to claim 16, wherein the navigation data is displayed in relation to the imaging data.

18. The navigation assistance system according to claim 17, wherein the navigation data is displayed in an augmented reality display positioned relative to a user.

19. The navigation assistance system according to claim 18, wherein the navigation data is at least partially based on a position of the augmented reality display relative to the patient.

20. The navigation assistance system according to claim 17, wherein the navigation data comprises trajectory information regarding the surgical instrument relative to the patient.

21. The navigation assistance system according to claim 20, wherein the navigation data is provided in real time relative to movements of the surgical instrument relative to the patient.

22. A navigation assistance system for use with a surgical instrument, comprising:
    at least one three-dimensional imaging sensor comprising a time of flight sensor located on the surgical instrument and disposed relative to a patient on which an operation is to be performed, wherein the at least one three-dimensional imaging sensor is operative to continually detect at least one reference anatomical feature of the patient in a surgical site adjacent to the surgical instrument to generate positioning data comprising a three-dimensional representation of the surgical site adjacent to the surgical instrument in a virtual reference space representing a location of the surgical instrument relative to the at least one reference anatomical feature;
    a data repository comprising imaging data corresponding to an imaging study of the patient, wherein the imaging data includes at least one imaged anatomical feature of the patient;

a navigation module that is operative to continually correlate the imaging data retrieved from the data repository with the positioning data to align the three-dimensional representation of the at least one reference anatomical feature to the at least one imaged anatomical feature in the virtual reference space and continually provide navigation data corresponding to a relative position of the surgical instrument with respect to the at least one imaged anatomical feature of the patient for navigation assistance of the surgical instrument in real-time during the operation; and a measurement system disposed at the surgical instrument that is operative to measure a displacement of a tool portion of the surgical instrument relative to a reference point to output a displacement signal and to measure a tool drive parameter that is characteristic of the tool portion acting on the patient to output a tool drive signal representative the tool drive parameter as the tool portion is advanced relative to anatomy of the patient;

wherein the navigation data is at least in part based on the displacement signal and the tool drive signal.

23. The navigation assistance system according to claim 22, wherein an approximate estimated surgical instrument location is provided to the navigation module.

24. The navigation assistance system according to claim 23, wherein the approximate estimated surgical instrument position is provided in relation to the imaging data.

25. The navigation assistance system according to claim 24, wherein the navigation module is operative to reduce the imaging data to be analyzed to an area of interest comprising less than an entirety of the imaging data based on the approximate estimated surgical instrument position.

26. The navigation assistance system according to claim 25, wherein the navigation data comprises an alert based on at least one of a position of the surgical instrument relative to the at least one imaged anatomical feature of the patient or a trajectory of the surgical instrument relative to the at least one imaged anatomical feature of the patient.

27. The navigation assistance system according to claim 26, wherein operation of the surgical instrument is at least in part based on the alert.

28. The navigation assistance system according to claim 27, wherein operation of the surgical instrument is ceased at least in part based on the alert.

29. A navigation assistance system for use in a surgical operation, comprising:

a surgical instrument comprising a tool portion;

a measurement system disposed at the surgical instrument that is operative to measure a displacement of the tool portion of the surgical instrument relative to a reference point to output a displacement signal and to measure a tool drive parameter that is characteristic of the tool portion acting on a patient to output a tool drive signal representative the tool drive parameter as the tool portion is advanced relative to anatomy of the patient;

at least one three-dimensional imaging sensor comprising a time of flight sensor disposed on the surgical instrument that is operative to continually detect at least one reference anatomical feature of the patient in a surgical site adjacent to the surgical instrument to generate positioning data comprising a three-dimensional representation of the surgical site adjacent to the surgical instrument in a virtual reference space representing a location of the surgical instrument relative to the reference anatomic feature;

a data repository comprising imaging data corresponding to an imaging study of the patient, wherein the imaging data includes at least one imaged anatomical feature of the patient; and a navigation module that is operative to continually correlate the imaging data retrieved from the data repository with the positioning data to align the three-dimensional representation of the at least one reference anatomical feature to the at least one imaged anatomical feature in the virtual reference space and continually provide navigation data, wherein the navigation data is at least in part based on the displacement signal and the tool drive signal, and wherein the navigation data corresponding to the relative position of the surgical instrument with respect to the at least one imaged anatomical feature of the patient for navigation assistance of the surgical instrument in real-time during the operation.

* * * * *